United States Patent [19]

Rosenblatt et al.

[11] Patent Number: 5,114,843
[45] Date of Patent: May 19, 1992

[54] HUMORAL HYPERCALCEMIC FACTOR ANTAGONISTS

[75] Inventors: Michael Rosenblatt, Ardmore; Roberta L. McKee; Michael P. Caulfield, both of Lansdale; Ruth F. Nutt, Green Lane, all of Pa.

[73] Assignee: Merck & Co., Inc., Rahway, N.J.

[21] Appl. No.: 662,340

[22] Filed: Feb. 25, 1991

Related U.S. Application Data

[63] Continuation of Ser. No. 341,530, Apr. 21, 1989, abandoned, which is a continuation-in-part of Ser. No. 191,513, May 9, 1988, abandoned.

[51] Int. Cl.$^5$ .................. G01N 33/567; C07K 7/10; A61K 37/02
[52] U.S. Cl. .................. 435/7.21; 435/7.2; 435/7.23; 435/7.1; 514/12; 530/324; 930/DIG. 820; 930/DIG. 821
[58] Field of Search .................. 435/7.21, 7.2, 7.23, 435/7.1; 530/324; 514/12; 930/DIG. 820, DIG. 821

[56] References Cited

U.S. PATENT DOCUMENTS

| | | | |
|---|---|---|---|
| 3,886,132 | 5/1975 | Brewer et al. | 530/324 |
| 4,086,196 | 4/1978 | Tregear | 530/324 |
| 4,423,037 | 12/1983 | Rosenblatt et al. | 530/324 |
| 4,771,124 | 9/1988 | Rosenblatt et al. | 530/324 |

FOREIGN PATENT DOCUMENTS

WO88/00596  1/1988  World Int. Prop. O.

OTHER PUBLICATIONS

Juppner et al., J. Biol. Chem. 1988, 263(18), 8557-60.
Kemp et al., Science, vol. 238, 1987, pp. 1568-1570.
Horiuchi et al., Science, vol. 238, 1987, pp. 1566-1568.
Rosol et al., Chem. Abs., vol. 109, 1988, 32522g.
Moseley et al., Proc. Natl. Acad. Sci. U.S.A., vol. 84, p. 5048 (1987).
Strewler et al., J. Clin. Invest., vol. 80, p. 1803, (1987).
Stewart et al., Biochem. Biophys. Res. Commun., vol. 146, p. 672 (1987).
Mangin et al., Proc. Natl. Acad. Sci. USA., vol. 85, p. 597 (1988).
Suva et al., Science, vol. 237, p. 893, (1987).
Rodan et al., J. Clin. Invest., vol. 72, p. 1511 (1983).
Stewart et al., Proc. Natl. Acad. Sci. U.S.A., vol. 80, p. 1454 (1983).
Strewler et al., J. Clin. Invest., vol. 71, p. 769 (1983).

Primary Examiner—Lester L. Lee
Assistant Examiner—T. D. Wessendorf
Attorney, Agent, or Firm—Salvatore C. Mitri; Charles M. Caruso

[57] ABSTRACT

The present invention relates to the use of peptide analogues as inhibitors of their respective naturally occurring peptides. The structure of the peptide analogues is exemplified by an internal region of the N-terminus of humoral hypercalcemic factor hHCF, and truncations thereof: hHCF(14-34)NH$_2$, hHCF(13-34)NH$_2$, hHCF(12-34)NH$_2$, hHCF(11-23)NH$_2$, hHCF(10-34)NH$_2$, hHCF(9-34)NH$_2$, hHCF(8-34)NH$_2$ and various amino acid substitutions.

4 Claims, No Drawings

HUMORAL HYPERCALCEMIC FACTOR ANTAGONISTS

RELATED APPLICATIONS

This is a continuation of application Ser. No. 341,530, filed Apr. 21, 1989, now abandoned, which is a continuation-in-part of U.S. Ser. No. 191,513, filed May 9, 1988, now abandoned.

BACKGROUND OF THE INVENTION

This invention relates to the use of peptide analogues useful in inhibiting the naturally occurring peptide in vivo and in vitro. These peptide analogues when administered to a vertebrate, such as mammals, block the activity of the peptide or other analogous molecules. These peptide analogues are also useful in vitro in combination with a bioassay for the naturally occurring peptide. The peptide analogues are useful in treating various diseases caused by excess of the naturally occurring peptide and in treating peptide dependent tumors. One example of this invention relates to the use and synthesis of humoral hypercalcemic factor (HCF) analogues useful for inhibiting the action of HCF both in vivo and in vitro.

Recently, several investigators isolated and obtained partial amino acid sequences of peptide derived from several different human tumors (lung squamous carcinoma, renal cell carcinoma, and breast carcinoma). J. M. Moseley et al., *Proc. Natl. Acad. Sci. U.S.A.* 84, 5048 (1987); G. J. Strewler et al., *J. Clin. Invest.*, 80, 1803 (1987); A. F. Stewart et al., *Biochem. Biophys. Res. Commun.* 146, 672 (1987); M. Mangin et al., *Proc. Natl. Acad. Sci. U.S.A.*, 85, 597 (1988). One group published the putative full-length peptide structure (141 amino acids) based on the complementary DNA (cDNA) nucleotide sequence. L. J. Suva et al., *Science* 237, 893 (1987).

This new factor has been named human "humoral hypecalcemic factor" (hHCF) and is considered to be related in biological effects to parathyroid hormone (PTH). HCF shows considerable homology to the biologically critical $NH_2$-terminal region of PTH. However, there are significant differences in the peptide sequences between PTH and HCF, and this new factor is the product of a different gene.

Previously, it had been proposed that tumors could secrete PTH ectopically and cause hypercalcemia of malignancy. However, messenger RNA for PTH was not found in such tumors. Several studies demonstrated that a PTH-like factor, physicochemically and immunologically distinct from PTH, is secreted by tumor cells. S. B. Rodan et al. *J. Clin. Invest.* 72, 1511 (1983); A. F. Stewart et al., *Proc. Natl. Acad. Sci. U.S.A.*, 80, 1454 (1983); G. J. Strewler et al., *J. Clin. Invest.* 71, 769 (1983). It was also known that this PTH-like factor stimulates adenylate cyclase in PTH target cells, and that this activity can be inhibited by PTH antagonists. Thus, it is presently considered that HCF is a factor that is responsible for hypercalcemia of malignancy by its secretion from the tumor and its altering effect on calcium metabolism.

It is, therefore, an object of the present invention to provide antagonists of HCF. If a peptide analogue of HCF could be constructed which would bind with the cell surface receptor of HCF, then the peptide analogue could be used to block the effect of the naturally occurring peptide. Thus, it is also an object of the present invention to provide peptide analogues useful for the treatment of hypercalcemia of malignancy.

Another object of the present invention is to provide novel HCF analogues. Other objects of the present invention are to provide methods of inhibiting the action of HCF through the administration of novel HCF analogues. Still another object of the invention is to provide HCF analogues wherein amino acid modifications result in binding to the cell surface receptors without activating a second messenger molecule. The above and other objects are accomplished by the present invention in the manner more fully described below.

SUMMARY OF THE INVENTION

The present invention provides peptides which comprise hHCF(14–34)$NH_2$, hHCF(13–34)$NH_2$, hHCF(12–34)$NH_2$, hHCF(11–34)$NH_2$, hHCF(10–34)$NH_2$, hHCF(9–34)$NH_2$, hHCF(8–34)$NH_2$.

Additionally, the present invention provides the above peptides wherein (a) $Ala^{34}$ is substituted by $Tyr^{34}$, and/or (b) $Phe^{23}$ is substituted by a hydrophobic amino acid selected from the group consisting of the D- or L-stereoisomers of Leu, Nle, Val, Tyr, Trp, beta-napthylalanine and alpha-naplthylalanine, and/or (c) any or each of $Asp^{10}$, $Lys^{11}$ or $Ile^{14}$ is substituted by any N-alkyl containing, or D- or L- stereoisomers of, any amino acid, in particular Asn, Leu or His.

The peptides hHCF(12–34)$NH_2$, hHCF(11–34)$NH_2$, hHCF(10–34)$NH_2$, hHCF(9–34)$NH_2$, hHCF(8–34)$NH_2$ wherein $Gly^{12}$ is substituted by an amino acid selected from the group consisting of the D- or L-stereoisomers of Trp, Pro, Ala, Aib, naphthyl Ala, alpha-MeTrp and NMe -Gly is also an aspect of the present invention. These peptides wherein (a) $Ala^{34}$ is substituted by $Tyr^{34}$, and/or (b) $Phe^{23}$ is substituted by a hydrophobic amino acid selected from the group consisting of the D- or L-stereoisomers of Leu, Nle, Val, Tyr, Trp, beta-naphthylalanine, alpha-naphthylalanine, and/or (c) any or each of $Asp^{10}$, $Lys^{11}$ or $Ile^{14}$ is substituted by any N-alkyl containing, or D- or L-stereoisomers of, any amino acid, in particular Asn, Leu or His.

Another feature of the present invention is the peptides which comprises [$Nle^{8,18}$] hHCF (8–34) $NH_2$ wherein (a) $Ala^{34}$ is substituted by $Tyr^{34}$, and/or (b) $Phe^{23}$ is substituted by an amino acid selected from the group consisting of the D- or L-stereoisomers of Leu, Nle, Val, Tyr, beta-napthylalanine and alpha-napthylalanine, and/or (c) $Gly^{12}$ is substituted by an amino acid selected from the group consisting of the D- or L-stereoisomers of Trp, Pro, Ala, Aib, naphtyl Ala, alpha-Me Trp and NMe Gly, and/or (d) any or each of $Asp^{10}$, $Lys^{11}$ or $Ile^{14}$ is substituted by any N-alkyl containing, or D- or L-stereoisomers of, any amino acid, in particular Asn, Leu or His. A preferred peptide ie hHCF(14–34)$NH_2$, and the peptide containing the substitutions indicated above where permissible.

Use of the terms "and/or" in the above description of the invention means that the substitutions described can be made singly or in any and all combinations described. For example, each of hHCF(14–34)$NH_2$,-[$Tyr^{34}$]hHCF(14–34)$NH_2$, [$Leu^{23}$]hHCF(7–34)$NH_2$, [$Leu^{23}$,$Tyr^{34}$]hHCR(14–34)$NH_2$, [$Leu^{11}$]hHCF-(7–34)$NH_2$, [$Leu^{11,23}$]hHCF(7–34) $NH_2$, [$Leu^{11,23}$,$Tyr^{34}$]hHCF(7–34)$NH_2$, as well as the other described combinations, are included within the present invention.

Any of the above-mentioned peptides can be used in a method of acting upon a HCF receptor which comprises administering an effective amount of such peptide to a mammal. Additionally, an in vitro bioassay of HCF, wherein a measured amount of such peptides inhibits binding of HCF to a HCF receptor in vitro is an aspect of the present invention. A pharmaceutical composition which comprises an effective amount of any such a peptide and a pharmaceutically acceptable carrier is another feature of this invention.

The present invention provides a method of inhibiting the action of HCF comprising the administration of therapetically effective amount of HCF analogues described above. The present invention also provides a method of treating osteoporosis or hypercalcemia comprising the administration of a therapeutically effective amount of a HCF analogue described above. A method of treating hyperparathyroidism comprising the administration of a therapeutically effective amount of the HCF analogues of this invention is also provided. A method of treating hyperparathyroidism expressed as a hypercalcemic crisis, renal failure or hypertension is also provided. A method of treating the disease state produced by a tumor or other cell overproducing a peptide hormone-like molecule and method of treating immune diseases wherein the disease state comprises inflammation, an allergic response, or hyperactive lymphocytes is also provided by the novel peptide analogues of the present invention.

DETAILED DESCRIPTION OF THE INVENTION

Various other objects, features and attendent advantages of the present invention will be more fully appreciated as the same becomes better understood from the following detailed description.

Extensive structure and activity studies have now led to the design of peptide analogues which have high binding affinity for their respective cell surface receptors while not stimulating the production of second messenger molecules.

HCF analogues with two to thirteen amino acids removed from the N-terminus produces an inhibitor which still binds with high affinity to the peptide hormone receptor without causing a change in cyclic AMP concentration.

The following is the 34-amino acid sequence of human humoral hypercalcemia factor (hHCF): Ala-Val-Ser-Glu-His(5)-Gln-Leu-Leu-His-Asp(10)-Lys-Gly-Lys-Ser-Ile(b 15)-Gln-Asp-Leu-Arg-Arg-(20)-Arg-Phe-Phe-Leu-His(25)-His-Leu-Ile-Ala-Glu(30)-Ile-His-Thr-Ala. Standard abbreviations well recognized in the peptide chemistry art are utilized herein. Aib represents an aminoisobutyrl substitutent.

Fragments of peptide, containing the region specific for binding to the cell surface receptor can be used as inhibitors or blocking agents. For HCF, it is considered that the N-terminal 34 amino acids are sufficient to define binding specificity to the cell surface receptor.

Use of the phrase "and/or" in the above description of the invention means that the indicated substitutions can be made singly or in any combination described. For one example, [D-Trp$^{12}$,Leu$^{11}$]hHCF(7-34)NH$_2$, [D-Trp$^{12}$]hHCF (7-34)NH$_2$ and [Leu$^{11}$]hHCF-(7-34)NH$_2$ are all within the scope of the present invention.

The presence of D-amino acids in peptide in place of L-amino acids sometimes results in a peptide resistant to catabolism. However, not all such substitutions result in an active peptide. Thus, such substitutions which result in active peptide are considered to be within the scope of the present invention. The utilization of D-amino acids in peptide hormone synthesis is described in the following publications herein incorporated by reference: Coltrera, et al., Biochemistry, 19:4380-4385, 1980; Rosenblatt et al, Biochemistry, 20:7246-7250, 1981. Additionally, substitutions of amino acids which are equivalent to the amino acids disclosed herein is considered to be within the scope of the present invention.

The balance of the description will be divided into two sections. Section I will describe the preparation and structure of inhibitors of peptide hormones, Section II will discuss the use of the peptide hormone inhibitors.

I. Preparation and Structure of Peptide Hormone Inhibitors

The technique of solid-phase peptide synthesis, developed by Merrifield ("Solid-Phase Peptide Synthesis", Advances in Enzymology, 32:221-296, (1969); G. Barany and R. B. Merrifield "Solid-Phase Peptide Synthesis" in The Peptides, volume 2, editors: E. Gross & J. Meienhofer (1980)) has been successfully employed in the synthesis of peptides including HCF. This method is based on the strategy of having the carboxyl terminus of the peptide linked covalently to a solid support. The desired peptide sequence is prepared by stepwise coupling of single amino acids to a peptide chain growing from the carboxyl toward the amino terminus. Coupling is typically achieved by activation of the carboxyl group of the amino acid being attached to the resin, which may have other potentially reactive groups blocked. Following addition of an amino acid to the growing polypeptide chain, and prior to further chain elongation, the alpha-amino (Boc) protecting group is typically removed. Because each amino acid is coupled by nearly the same series of reactions, the need for elaborate strategies in the synthesis is minimized. Solubility is not a major issue during synthesis, because the peptide is linked to a solid support. This method is rapid and it can be utilized by a single worker. It is very convenient for the synthesis of multiple analogues with amino-terminal substitutions, because a single synthesis can be branched in multiple directions near the amino terminus, thereby creating many analogues varying only in the amino terminal region.

II. Use of Peptide Inhibitors

The method of inhibiting the action of HCF peptide comprises the administration of a therapeutically effective amount of any HCF peptide analogue. These peptide analogues retain specificity for the cell surface receptor without stimulating a physiological response. This method of use applies to the entire peptide or its analogue, or to a fragment of the peptide or analogue containing the receptor binding site.

The use of peptide analogues is exemplified by HCF analogues. The HCF is of human origin but HCF of bovine, rat or any mammalian source may prove to be equivalent to the human HCF. The analogue may contain all the amino acids indicated, or additionally truncations or elongations. Individual amino acids can be substituted to improve biological or chemical stability.

The peptide analogues of this invention can be used in vitro to measure the concentration of naturally occurring peptide. This bioassay procedure is illustrated by a bioassay for HCF. The unknown concentration of HCF in a solution can be determined by measuring the amount of HCF analogue required to inhibit its binding to the HCF cell surface receptor. The concentration of HCF analogue required to block the action of HCF is a direct indicator of the HCF concentration.

HCF analogues can be used to diagnose the etiology of or to treat osteoporosis or hypercalcemia through the administration of a therapeutically effective amount of the HCF analogues of this invention. Similarly, hyperparathyroidism and other aspects of hyperparathyroidism, such as a hypercalcemic crisis, renal failure of hypertension can be treated through the administration of the HCF analogues of this invention.

Tumors and other aberrant cell growth often produce hormone-like substances causing a disease state. The use of peptide analogues to block stimulation caused by such hormone-like substances can result in the alleviation of the disease state. An example of this is the humoral hypercalcemic factor of malignancy. Therefore, the HCF peptide analogues of the present invention can be administered to treat diseases caused by aberrant production of hormone-like substances.

The peptide analogues of this invention exhibit both oral and parenteral activity and can be formulated in dosage forms for oral, parenteral, intra-nasal, or topical administration. Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluent. In the case of capsules, tablets, and pills, the dosage forms may also comprise buffering agents. Tablets and pills can additionally be prepared with an enteric coating.

Liquid dosage forms for oral administration include pharmaceutically acceptable emulsion, solutions, suspensions, syrups and elixers containing inert diluents commonly used in the pharmaceutical art. Besides inert diluents, such compositions can also include adjuvants, such as wetting agents, emulsifying and suspending agents, and sweetening. Preparations according to this invention for parenteral administration include sterile aqueous or non-aqueous solutions, suspensions or emulsions. Examples of non-aqueous solvents or vehicles are propylene glycol, polyethylene glycol, vegetable oils such as olive oil and injectable organic esters such as ethyloleate.

The dosage of active ingredient in the compositions of this invention may be varied; however it is necessary that the amount of the active ingredient shall be such that a suitable dosage form is obtained.

The selected dosage form depends upon the desired therapeutic effect, on the route of the administration, and on the duration of the treatment.

Obviously, numerous modifications and variations of the present invention are possible in light of the above teachings. It is therefore to be understood that within the scope of the appended claims, the invention may be practiced otherwise than as specifically described herein.

EXAMPLE 1

Synthesis and Purification of Peptide Analogues of HCF

Analogues of HCF, where prepared by a modification of the solid-phase method of Merrifield. Syntheses were performed using an Applied Biosystems 430A Synthesizer. 4-Methylbenzhydrylamine hydrochloride resin (polystyrene-1% by divinylbenzene, USB) was employed as the solid support in order to effect the carboxyamide (CONH2) COOH-terminal modification.

The tertiary butyloxycarbonyl (Boc) group was used to protect the alpha -amino group of each amino acid during coupling. Side-function protection was afforded as follows: (a) the hydroxyl group of serine was protected as the O-benzyl ether (Bzl); (b) the hydroxyl group of tryosine as the 0-2,6-dichlorobenzyl ether (DCB) or p-bromobenzyloxycarbonyl ester (Brz); (c) the carboxyl group of glutamic and aspartic acid as the benzyl (BZ) or cyclohexyl ester (Chx); (d) the imidazole nitrogen of histidine by the benzyloxymethyl (BOM) and the guanidine function of arginine was protected by the p-toluene-sulfonyl (TOS) group, and the indole imine by formyl groups (For); and (e) the Lysine epsilon amino group by 2-chloro-benzyloxycarboxyl (ClZ). All amino acids were obtained from Applied Biosystems, Inc., Peninsula Laboratories, or Bachem Chemicals.

The peptide-resin synthesis were carried out using Applied Biosystems, Inc. specified protocols. Double couplings were carried out for the incorporation of each amino acid. After the final coupling of each of the arginines (residues 18-21) the remaining free amino groups were acetylated to prevent generation of deletion peptides. Deprotection times with trifluoroacetic acid (TFA) were extended 6 minutes over manufacturer protocols.

The peptide was cleaved from the copolymer resin with simultaneous removal of the side-chain protecting groups similar to the 2 step HF cleavage procedure described by Tam, J.A.C.S. 105: 6442-6455 (1983). In the first HF step the following ratios of reagents were used: 5% p-cresol, 5% p-thiocresol, 65% dimethyl sulfide and 25% HF. 10 ml of mixture per gram of peptide-resin was used for 2 hours at 0° C. In the second HF step the following ratio of reagents were used: 5% p-cresol, 5% p-thiocresol and 90% HF. The cleavage was carried out for 75 min. at 0° C. After removal of HF the peptide-resin mixture was washed with anhydrous ether to remove scavenger. The peptide was then extracted with 50% acetic acid and water. The washes were combined and chromatographed using Sephadex G-50F, eluting with 50% HOAc.

After lyophilization, the partially purified peptide was chromatographed by reverse phase HPLC (Vydac $C_4$ bonded silica, 15 $\mu$ particle size, 300A pore size, using aqueous acetonitrile gradient containing 0.1% TFA).

EXAMPLE 2

HCF Binding Assay Results

HCF analogues were analysed in a new receptor assay (Goldman et al., Endocrinol. (1988) 123: 1468-1475) which modified the assay reported in Rosenblatt et al., Endocrin. 107: 545-550 (1980). The binding assay used [Nle$^{8,18}$($^{125}$I)-Tyr$^{34}$]bPTH (1-34)NH$_2$ which was purified by HPLC (Novapak $C_{18}$, 32-35% CH$_3$CN in 0.1% TFA) and was stored as aliquots in 25 mM TrisHCl/1%BSA at $-70°$ C. Bovine renal cortical plasma membranes were incubated with radioligand (25,000 cpm) in the absence or presence of HCF analogues in a Tris-containing buffer (250 $\mu$l) for 30 min. at 21° C. Once equilibrium was reached, bound and free radioligand were separated by centrifugation.

High specific binding (85%) to bovine renal cortical membranes was obtained consistently.

| Structure | Binding $K_I$ (nM) |
| --- | --- |
| hHCF(14–34)NH$_2$ | 1400 ± 83 |
| [D-Trp$^{12}$]hHCF(10–34)NH$_2$ | 403 ± 251 |

EXAMPLE 3

HCF analogues were analyzed in a bovine renal cortical membrane adenylate cyclase assay as described in Horiuchi et al., *Science* 238, 1566 (1987); Goldman et al., *Endocrin* (1988) 123(5): 1468–1475. 3nM [Nle$^{8,18}$,Tyr$^{34}$]bPTH(1–34) NH$_2$ was used to stimulate adenylate cyclase.

| Structure | Binding $K_I$ (nM) |
| --- | --- |
| hHCF(14–34)NH$_2$ | 6,600 ± 1300 |
| [D-Trp$^{12}$]hHCF(10–34)NH$_2$ | 2,365 ± 650 |

EXAMPLE 4

HCF analogues were analyzed in a rat osteosarcoma cell line, ROS 17/2.8, for the ability to inhibit cAMP stimulation by 1nM [Nle$^{8,18}$, Tyr$^{34}$]bPTH(1–34) NH$_2$ by the method described by McKee, R. et al., Endocrinol. (1988) 122(6): 3008–10.

| Structure | Binding $K_I$ (nM) |
| --- | --- |
| hHCF(14–34)NH$_2$ | 2040 ± 160 |

What is claimed is:

1. A peptide selected from the group consisting of hHCF(14–34)NH$_2$ or hHCF(10–34)NH$_2$ wherein Gly$^{12}$ in each of said peptides is substituted by an amino acid which is a member selected from the group consisting of the D- or L-stereoisomers of Trp, Pro, Ala, Aib, napthyl Ala, alpha-Me Trp and N Me Gly.

2. A peptide of claim 1 which is [D-Trp$^{12}$]hHCF(10–34)NH$_2$.

3. An invitro bioassay of HCF, wherein radiolabeled HCF together with an effective amount of the peptide of claim 1 reacts with a HCF receptor, present in animal cells or membranes, and following the reaction, the amount of radiolabeled HCF bound to the receptor is measured.

4. A pharmaceutical composition which comprises an effective amount of a peptide of claim 1 and a pharmaceutically acceptable carrier.

* * * * *